US012629073B2

(12) United States Patent
Woody et al.

(10) Patent No.: US 12,629,073 B2
(45) Date of Patent: May 19, 2026

(54) SYSTEM AND METHOD FOR PROVIDING NEUROFEEDBACK FROM STEADY-STATE VISUAL EVOKED POTENTIALS TO TARGET AFFECT-BIASED ATTENTION FOR TREATING THERAPEUTIC OUTCOMES SUCH AS ANXIETY AND DEPRESSION

(71) Applicants: UNIVERSITY OF PITTSBURGH—OF THE COMMONWEALTH SYSTEM OF HIGHER EDUCATION, Pittsburgh, PA (US); UPMC, Pittsburgh, PA (US); NORTHEASTERN UNIVERSITY, Boston, MA (US)

(72) Inventors: Mary L. Woody, Pittsburgh, PA (US); Murat Akcakaya, Pittsburgh, PA (US); Sarah Ostadabbas, Watertown, MA (US); Rebecca Price, Pittsburgh, PA (US); Xiaofei Huang, Lynnfield, MA (US); Richard T. Gall, Pittsburgh, PA (US); Anna Wears, Pittsburgh, PA (US); Nastasia O. McDonald, Pittsburgh, PA (US); Jennifer Mak, Pittsburgh, PA (US)

(73) Assignees: University of Pittsburgh—Of the Commonwealth System of Higher Education, Pittsburgh, PA (US); UPMC, Pittsburgh, PA (US); Northeastern University, Boston, MA (US)

( * ) Notice: Subject to any disclaimer, the term of this patent is extended or adjusted under 35 U.S.C. 154(b) by 291 days.

(21) Appl. No.: 18/469,782

(22) Filed: Sep. 19, 2023

(65) Prior Publication Data

US 2024/0090810 A1 Mar. 21, 2024

Related U.S. Application Data

(60) Provisional application No. 63/376,494, filed on Sep. 21, 2022.

(51) Int. Cl.
A61B 5/16 (2006.01)
A61B 5/00 (2006.01)
(Continued)

(52) U.S. Cl.
CPC .............. *A61B 5/168* (2013.01); *A61B 5/378* (2021.01); *A61B 5/6803* (2013.01);
(Continued)

(58) Field of Classification Search
CPC ....... A61B 5/168; A61B 5/378; A61B 5/6803; A61B 5/7257
See application file for complete search history.

(56) References Cited

U.S. PATENT DOCUMENTS 9,302,179 B1 * 4/2016 Merzenich ............... G09B 5/00
10,342,472 B2 * 7/2019 Simpson ................ A61B 5/168
(Continued)

FOREIGN PATENT DOCUMENTS

CN 109828664 B 1/2019

*Primary Examiner* — Eric F Winakur
(74) *Attorney, Agent, or Firm* — Philip E. Levy; Eckert Seamans Cherin & Mellott, LLC

(57) ABSTRACT

A neurofeedback system includes an EEG apparatus, a presentation apparatus and a controller. The controller is configured to: (i) cause the presentation apparatus to display an overlaid image to the user that comprises a first image flickering at a first frequency and a second image flickering at a second frequency different than the first frequency, the first image being an affective distractor stimulus image and the second image being a task-relevant stimulus image, (ii) receive from the EEG apparatus a number of first steady-state visual evoked potential (SSVEP) signals generated in (Continued)

response the first image of the overlaid image and a number of second SSVEP signals generated in response the second image of the overlaid image, and (iii) calculate feedback indicative of how much attention of the was user allocated to the task-relevant stimulus image versus how much attention of the user was allocated to the affective distractor stimulus image.

24 Claims, 3 Drawing Sheets

(51) Int. Cl.
    *A61B 5/378*          (2021.01)
    *A61B 90/00*         (2016.01)
(52) U.S. Cl.
    CPC ............ *A61B 5/7257* (2013.01); *A61B 90/36*
              (2016.02); *A61B 2090/365* (2016.02)

(56)                  References Cited

U.S. PATENT DOCUMENTS

| | | | |
|---|---|---|---|
| 2011/0004412 A1 | 1/2011 | Shahaf et al. | |
| 2014/0171757 A1* | 6/2014 | Kawato .................. | A61B 5/377 |
| | | | 600/545 |
| 2019/0159716 A1* | 5/2019 | Alailima ................ | A61B 5/165 |

* cited by examiner

1

SYSTEM AND METHOD FOR PROVIDING NEUROFEEDBACK FROM STEADY-STATE VISUAL EVOKED POTENTIALS TO TARGET AFFECT-BIASED ATTENTION FOR TREATING THERAPEUTIC OUTCOMES SUCH AS ANXIETY AND DEPRESSION

CROSS REFERENCE TO RELATED APPLICATIONS

This application claims priority to U.S. Provisional Patent Application Ser. No. 63/376,494, filed on Sep. 21, 2022 and titled "System and Method for Providing Neurofeedback from Steady-State Visual Evoked Potentials to Target Affect-Biased Attention", the disclosure of which is incorporated herein by reference.

GOVERNMENT CONTRACT

This invention was made with government support under grant #MH119225 awarded by the National Institutes of Health (NIH), and grant #s 1915065 and 1915083 awarded by National Science Foundation (NSF). The government has certain rights in the invention.

FIELD OF THE INVENTION

The disclosed concept relates generally to neurofeedback systems and methods, and, in particular, to a system and method for providing neurofeedback to an individual based on steady-state visual evoked potentials (SSVEPs) to target affect-biased attention.

BACKGROUND OF THE INVENTION

Attention is responsible for curating ongoing perceptions of the environment and its predominant characteristics (e.g., threat vs. safety; punishment vs. reward), which contributes to affective states. For this reason, biases in attention to emotional stimuli (i.e., affect-biased attention) are a proposed mechanism underlying depression and anxiety disorders. Attempts have been made to therapeutically train patients to prioritize "goal-directed" attention to task-relevant stimuli by training attention away from distracting "stimulus-driven" negative stimuli using repeated, automated practice during behavioral tasks. However, most previous attention modification interventions are limited by problems with reliability and interpretability, and there is a need to increase the robustness and precision of these interventions.

Because of the precision of brain-based measurement, neurofeedback is a promising modality for targeting affect biased attention. Neurofeedback has been effective in shaping behavior through brain-based feedback about attention, which allows patients to immediately and precisely adjust their attention to emotional information. However, past neurofeedback paradigms used cost-prohibitive functional magnetic resonance imaging (fMRI) procedures, limiting their translation to the clinic.

SUMMARY OF THE INVENTION

In one embodiment, a system for providing neurofeedback to a user to target affect-biased attention is provided. The system includes an electroencephalogram (EEG) apparatus structured and configured to generate a number of EEG signals when coupled to a head of the user, a presentation apparatus structured and configured to visually display a plurality of images to the user, and a controller coupled to the EEG apparatus and the presentation apparatus. The controller is structured and configured to: (i) cause the presentation apparatus to display an overlaid image to the user, wherein the overlaid image comprises a first image flickering at a first frequency overlaid with a second image flickering at a second frequency different than the first frequency, the first image being an affective distractor stimulus image and the second image being a task-relevant stimulus image, (ii) receive from the EEG apparatus a number of first steady-state visual evoked potential (SSVEP) signals generated in response the first image of the overlaid image and a number of second SSVEP signals generated in response the second image of the overlaid image, and (iii) calculate feedback based on at least the number of first SSVEP signals and the number of second SSVEP signals, the feedback being indicative of how much attention of the was user allocated to the task-relevant stimulus image versus how much attention of the user was allocated to the affective distractor stimulus image.

In another embodiment, a method for providing neurofeedback to a user to target affect-biased attention is provided. The method includes (i) displaying an overlaid image to the user, wherein the overlaid image comprises a first image flickering at a first frequency overlaid with a second image flickering at a second frequency different than the first frequency, the first image being an affective distractor stimulus image and the second image being an affective distractor stimulus image, (ii) receiving a number of first steady-state visual evoked potential (SSVEP) signals generated in response the first image of the overlaid image and a number of second SSVEP signals generated in response the second image of the overlaid image, and (iii) calculating feedback based on at least the number of first SSVEP signals and the number of second SSVEP signals, the feedback being indicative of how much attention of the was user allocated to the task-relevant stimulus image versus how much attention of the user was allocated to the affective distractor stimulus image.

BRIEF DESCRIPTION OF THE DRAWINGS

A full understanding of the invention can be gained from the following description of the preferred embodiments when read in conjunction with the accompanying drawings in which.

DETAILED DESCRIPTION OF THE INVENTION

Figure 1:
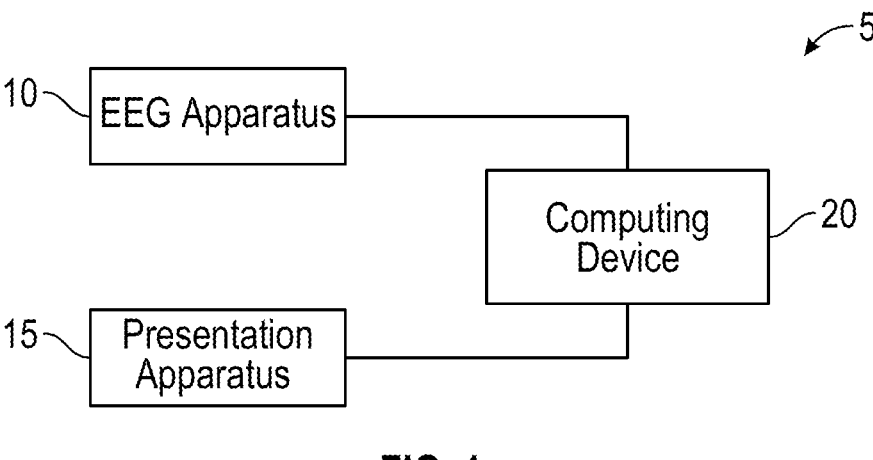
FIG. 1 is a schematic diagram of a neurofeedback system according to an exemplary embodiment of the disclosed concept.

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs.

As used herein, "directly coupled" means that two elements are directly in contact with each other.

As used herein, the term "number" shall mean one or an integer greater than one (i.e., a plurality).

As used herein, the terms "component" and "system" are intended to refer to a computer related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers. While certain ways of displaying information to users are shown and described with respect to certain figures or graphs as screenshots, those skilled in the relevant art will recognize that various other alternatives can be employed.

As used herein, the term "controller" shall mean a programmable analog and/or digital device (including an associated memory part or portion) that can store, retrieve, execute and process data (e.g., software routines and/or information used by such routines), including, without limitation, a field programmable gate array (FPGA), a complex programmable logic device (CPLD), a programmable system on a chip (PSOC), an application specific integrated circuit (ASIC), a microprocessor, a microcontroller, a programmable logic controller, or any other suitable processing device or apparatus. The memory portion can be any one or more of a variety of types of internal and/or external storage media such as, without limitation, RAM, ROM, EPROM(s), EEPROM(s), FLASH, and the like that provide a storage register, i.e., a non-transitory machine readable medium, for data and program code storage such as in the fashion of an internal storage area of a computer, and can be volatile memory or nonvolatile memory.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As described in detail herein, the disclosed concept provides a more cost-effective electroencephalogram (EEG) modality, using steady-state visual evoked potentials (SSVEPs), to target and modify affect-biased attention. EEG-derived SSVEPs provide a temporally-sensitive biological index of competition between stimulus-driven and goal-directed attention at the level of neuronal populations in the visual cortex and can distinguish attention to competing visual stimuli even when they completely overlap in time and space. The disclosed concept, in the non-limiting exemplary embodiment, provides an SSVEP-based neurofeedback protocol in an extended reality (XR) setting that combines EEG measurements recorded in response to visual stimuli presented through augmented reality (AR) and/or virtual reality (VR) technology for real-time affect-biased attention detection and neurofeedback implementation. The use of XR in a clinical setting allows patients to see their environment while tasks or alerts appear in their visual field in an overlay fashion. This makes the environment more comfortable and intuitive to control than an entirely virtual space.

FIG. 1 is a schematic diagram of a neurofeedback system 5 according to an exemplary embodiment of the disclosed concept. As described in detail herein, neurofeedback system 5 is structured and configured to provide neurofeedback to a user for modifying affect-biased attention based on EEG signals obtained from a user that are generated in response to certain overlaid images as described herein. Thus, as seen in FIG. 1, neurofeedback system 5 includes an EEG apparatus 10 that is structured and configured to record EEG signals, such as SSVEP signals, from a user, and a presentation apparatus 15 that is structured and configured to display images to the user as described herein. In addition, EEG apparatus 10 and presentation apparatus 15 are coupled to a computing device 20.

Computing device 20 may be, for example and without limitation, a PC, a laptop computer, a tablet computer, a smartphone, or any other suitable device structured and configured to perform the functionality described herein. Computing device 20 is structured and configured to control presentation apparatus 15 as described herein to display certain overlaid images to the user. In particular, each overlaid image comprises a first image flickering at a first frequency, f1, to evoke SSVEPs frequency tagged to the first image, that is overlaid with a second image flickering at a second frequency, f2, different than the first frequency, to evoke SSVEPs frequency tagged to the second image. In the exemplary embodiment, the first image is an affective distractor stimulus image, such as a sad and/or angry face, and the second image is a goal directed task-relevant stimulus image, such as a Gabor patch (which is a patch of parallel lines). Computing device 20 is also structured and configured to receive from the EEG apparatus 10 certain EEG signals that are generated in response to the displayed overlaid images, including certain SSVEP signals. Computing device 20 is further structured and configured to generate feedback for the user based on the received EEG signals, wherein the feedback is indicative of how much attention of the user was allocated to each of the individual images that make up the overlaid image.

Figure 2:
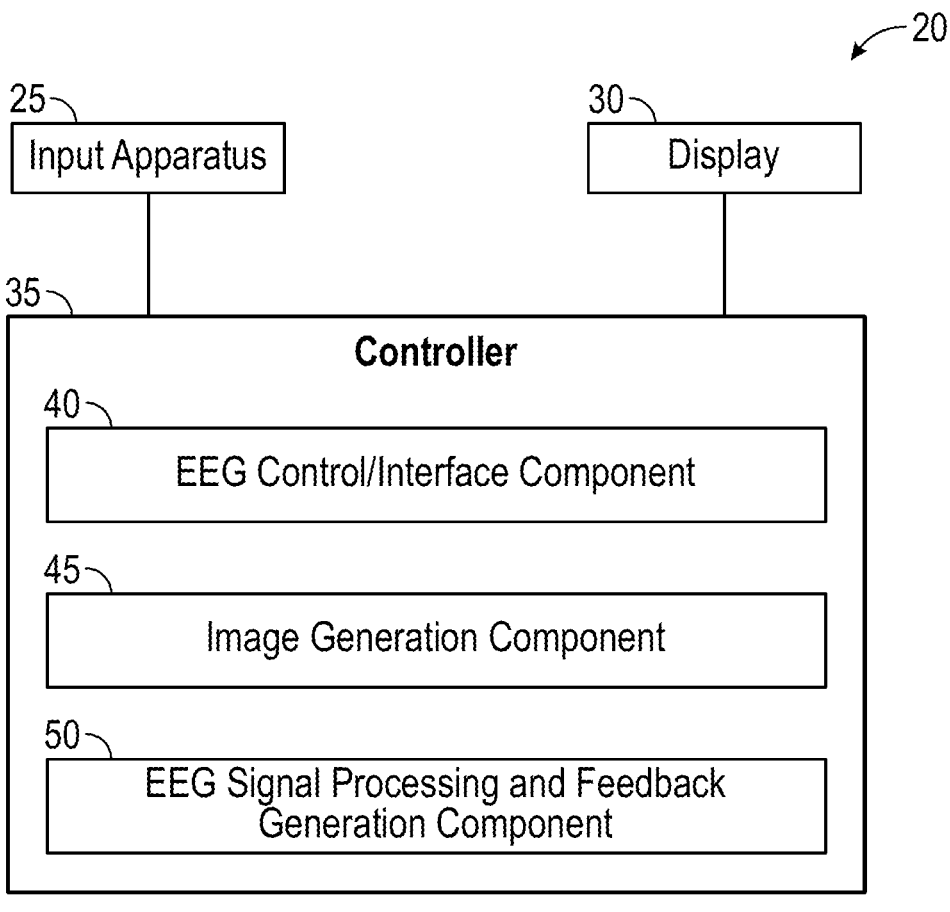
FIG. 2 is a block diagram of a computing device of the system of FIG. 1 according to one exemplary embodiment.

FIG. 2 is a block diagram of computing device 20 according to one exemplary embodiment. As seen in FIG. 2, the exemplary computing device 20 is a PC or laptop computer and includes an input apparatus 25 (such as a keyboard), a display 30 (such as an LCD), and a controller 35. A user is able to provide input into controller 35 using input apparatus 30, and controller 35 provides output signals to display 30 to enable display 30 to display information to the user, including the images and feedback described herein. The memory portion of controller 35 has stored therein a number of routines that are executable by a processor of controller 35. One or more of the routines implement (by way of computer/processor executable instructions) at least one embodiment of the method discussed in detail herein for providing neurofeedback to a user for modifying affect-biased attention. Controller 35 thus includes an EEG control/interface component 40 for interfacing with EEG apparatus 10 and receiving signals therefrom, an image generation component 45 for creating the overlaid images as described herein, and an EEG signal processing and feedback generation component 50 for processing the received EEG signals and generating the feedback as described in detail herein.

Figure 3:
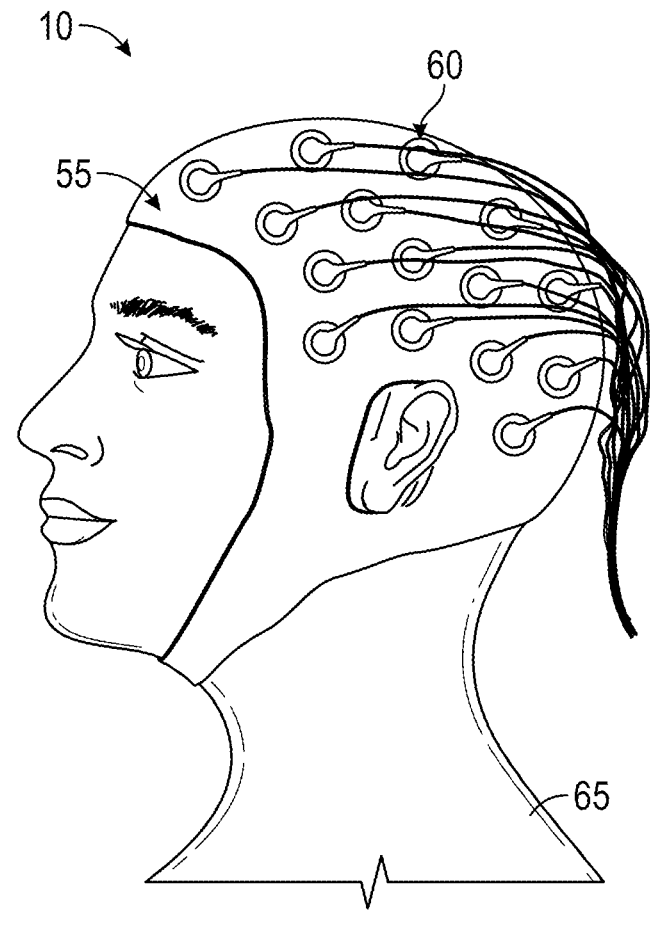
FIG. 3 is a schematic diagram of EEG apparatus 10 according to a non-limiting exemplary embodiment of the disclosed concept.

FIG. 3 is a schematic diagram of EEG apparatus 10 according to a non-limiting exemplary embodiment of the disclosed concept. As seen in FIG. 3, in this embodiment, EEG apparatus 10 includes an EEG cap 55 having a plurality of electrodes 60 coupled thereto for collecting EEG signals from an exemplary user 65. In addition, it should be noted that SSVEPs are typically measured over the occipital scalp region. Thus, in the exemplary embodiment, channels of EEG cap 55 corresponding to the occipital region are used in to calculate SSVEPs, such as by averaging the signals from those channels. It will be appreciated that the embodiments described in this paragraph are meant to be exemplary only, and that other forms of an EEG apparatus 10 may also be used within the scope of the disclosed concept.

Figure 4:
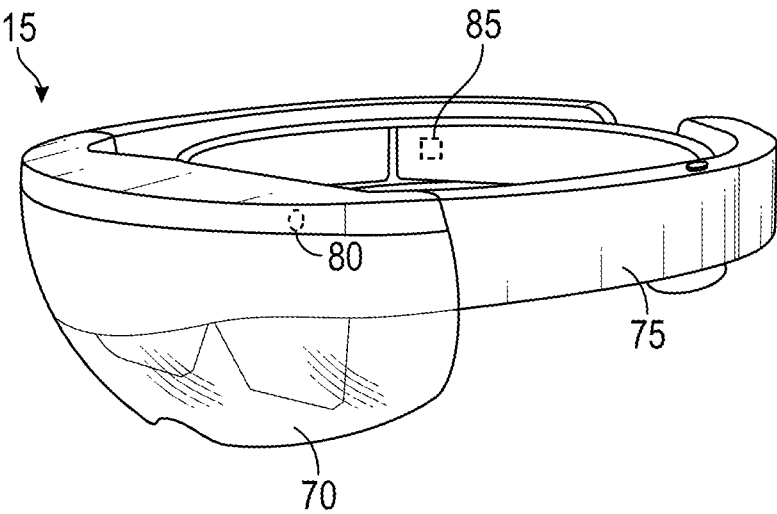
FIG. 4 is a schematic diagram of presentation apparatus of the system of FIG. 1 according to the non-limiting exemplary embodiment of the disclosed concept.

FIG. 4 is a schematic diagram of presentation apparatus 15 according to the non-limiting exemplary embodiment of the disclosed concept. As seen in FIG. 4, presentation apparatus 15 in this embodiment comprises a head mounted display (HMD) device that includes a display device 70 and a frame 75 that wraps around the head of a user to position the display device 70 close to the user's eyes when providing an extended reality (XR; encompassing both augmented and/or virtual reality) experience to the user. Any suitable display technology and configuration may be used to display images via the display device 70. For a VR experience, the display device 70 may be a non-see-through light-emitting diode (LED) display, a liquid crystal display (LCD), or any other suitable type of opaque display. In some cases, an outwardly facing camera 80 may be provided that captures images of the surrounding environment, and these captured images may be displayed on the display along with computer generated images that augment the captured images of the real environment. For an AR experience, the display device 70 may be at least partially transparent so that the user of the HMD device may view physical, real-world objects in the physical environment through one or more partially transparent pixels displaying virtual object representations. For example, the display device 70 may include image-producing elements such as, for example, a see-through organic light-emitting diode (OLED) display. Finally, the HMD device of this embodiment includes a controller 85 for controlling operation of the device, in particular in response to signals from computing device 20. In the preferred, non-limiting exemplary embodiment of the disclosed concept, presentation apparatus 15 is an AR device such as that just described.

Figure 5:
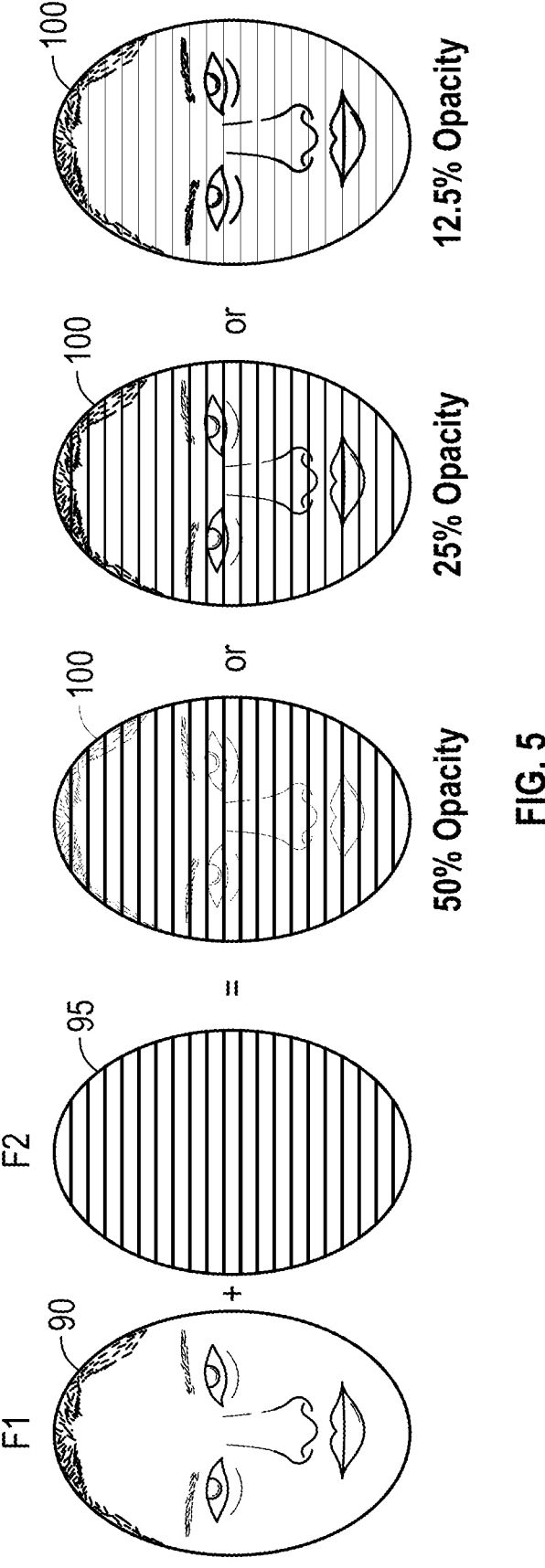
FIG. 5 shows an exemplary affective distractor stimulus image, a task-relevant stimulus image, and sample overlaid images according to an embodiment of the disclosed concept.

In general, neurofeedback system 5 operates by providing feedback to a user during performance of a number of task trials during which the user is presented with competing visual stimuli on presentation apparatus 15 comprising an affective (i.e., emotional) distractor stimulus and a task-relevant stimulus. Each trial is directed toward assessing the user's goal directed attention to the task-relevant stimulus as compared to the user's stimulus-driven attention to the affective distractor stimulus. Thus, in each trial, an overlaid image 100 comprising two competing visual stimuli are provided to the user on presentation apparatus 15 for a predetermined period of time, such as five seconds. The competing visual stimuli in each trial include (i) an affective distractor stimulus image (such as an angry or sad face), and (ii) a task-relevant stimulus image (such as a semitransparent Gabor patch). The competing visual stimuli are presented to the user as an overlaid image in which the affective distractor stimulus image is flickered at a first frequency, f1, to evoke SSVEPs frequency tagged to the affective distractor stimulus image, and the task-relevant stimulus image is flickered at a second frequency, f2, that is distinct from f1, to evoke SSVEPs frequency tagged to the task-relevant stimulus image. This is illustrated in FIG. 5, which shows an exemplary affective distractor stimulus image 90 in the form of a sad or angry face flickered at frequency f1, and a task-relevant stimulus image 95 in the form of a semitransparent Gabor patch of a given opacity flickered at frequency f2. As seen in FIG. 5, those two stimulus images 90, 95 will produce an overlaid image 100 as shown, with the specifics of the overlaid image depending upon the opacity of the Gabor patch. FIG. 5 shows three different exemplary overlaid images 100 for Gabor patch opacities of 50%, 25%, and 12.5%, respectively.

Furthermore, during each trial, while the overlaid image is presented to the user on presentation apparatus 15 as just described, EEG apparatus 10 measures the EEG response of the user and generates a number of EEG signals for the trial that are provided to computing device 20. At the end of each trial, computing device 20 calculates/determines the stimulus-driven attention of the user to the affective distractor stimulus image 90 (e.g., the sad or angry face) and the goal-directed attention to the task-relevant stimulus image 95 (e.g., the Gabor patch) using a Fourier transform (FT) at the competing frequency tags (f1 and f2). The proportion of attention allocated to the task-relevant stimulus image versus the affected distractor stimulus image at any given time point is, in the exemplary embodiment, calculated using time and spectral features using machine learning algorithms, including support vector machines (SVM). Specifically, the spectral features are calculated through Fourier transform (FT) at competing frequency tags comprising the first frequency and the second frequency (i.e., f2 and f1) and integer multiples of each frequency value, and the time features are calculated time-locked to the presentation of each image. This results in an SSVEP competition score ranging from 0 to 1. Scores greater than 0.5 in this embodiment indicate that the task-relevant stimulus image won the competition for attention during the trial, whereas scores less than or equal to 0.5 indicate that the affective distractor stimulus image won the competition for attention during the trial. In the exemplary embodiment, after each trial, feedback comprising an indication of which image won the competition and/or how much attention was allocated to the task-relevant stimulus image versus the emotional distractor stimulus image in the form of the SSVEP competition score is provided to the user on presentation apparatus 15.

In one particular, non-limiting exemplary embodiment of the disclosed concept, a three-phase affect-biased attention training protocol is provided that employs the overlaid images and the SSVEP based signals and analysis described herein to provide neurofeedback to the user. As described in more detail below, this exemplary protocol includes the following three phases: (i) a baseline phase, (ii) a training phase, and (iii) a mastery phase.

In the baseline phase, the user completes 30 trials as described herein. In each of those trials, the task-relevant stimulus image part of the overlaid image is provide at a 50% opacity. During this baseline phase, no feedback is given to the user.

The training phase follows the baseline phase. In the training phase, the user completes three training epochs, where each epoch contains 30 trials as described herein (with 50% opacity of the task-relevant stimulus image), with discrete feedback being presented to the user after each trial in the form of the SSVEP competition score. As described herein, the SSVEP competition score tells the user which stimulus (e.g., Gabor or face) has "won" the competition for attention during that trial. At the end of the second and third epochs, the user also receives feedback comparing their performance on the current epoch to the previous epoch. If the user increased the number of trials where the task-relevant stimulus image (e.g., Gabor) "won", then they are told something like "You're getting better, keep up the hard work!". Otherwise, the user is told something like "Please keep practicing to improve your performance."

The mastery phase follows the training phase. In the mastery phase, trials as described herein are administered to the user across three levels that progress in difficulty by reducing the opacity of the task-relevant stimulus image (e.g., Gabor). Specifically, in the first level, 50% opacity is used, in the second level 25% opacity is used, and in the third level, 12.5% opacity is used. Within each level, a maximum of three epochs are completed, with each epoch including a maximum of 30 trials. In addition, during each level, the SSVEP competition score is calculated but not presented to the user. Rather, during each level, once the user crosses a "mastery" threshold within any epoch or level (as indicated by the SSVEP competition score(s)), then the epoch or level is concluded; otherwise, epochs or levels concluded once the maximum number of trials or epochs were completed. More specifically, in the exemplary embodiment, in each level a running average of the calculated SSVEP competition scores is maintained. Once the user's average score crosses a predetermined "mastery" threshold (e.g., 0.55, after at least 2 trials), then mastery of that epoch is marked. After at least 2 epochs in any level are marked as "mastered", then the level concluded. If mastery is not demonstrated by the end of the maximum number of trials per epoch (30) or epochs per level (3), then the epoch or level is still concluded but mastery is not marked. If mastery of a level is marked, then the user is allowed to move on to the more difficult subsequent level. Otherwise, the user repeats the level. The mastery phase concludes once three levels are completed (regardless of whether mastery of each level is marked).

Moreover, through experimental testing, the inventors have determined that SSVEP competition scores may be most advantageously calculated for each trial using a certain calculation method and certain frequency ranges. Specifically, SSVEP competition scores may be most advantageously calculated based on extracting the average power from the respective face and Gabor frequency ranges, wherein the frequency ranges are $f_{fund}-1.5<f<f_{fund}+1.5$, and wherein $f_{fund}$ represents the fundamental frequency of face or Gabor, respectively.

Finally, in one particular non-limiting exemplary embodiment, a subject-specific support vector machine (SVM) was developed to determine whether a subject was attending to the Gabor or the face at the level of a single trial. Three different EEG features were tested: the full power spectral density (PSD), the power of EEG signals from different frequency bands around the different harmonics of the Gabor and the face normalized by the total power of the signal (Power banks), and the correlation of the EEG signal to a cosine signal oscillating at the frequencies of the different harmonics of the Gabor and the face (Cosine correlation). The features were extracted from the occipital scalp region (channels O1, O2, and Oz). Along with the different features, a forward feature selection method was used to optimize the model. The forward feature selection method randomly selected features iteratively until a criterion was met; in this case, the loss was used. When using the forward feature selection method, the number of features was maximized by selecting the largest number of harmonics to allow the forward feature selection to pick from the largest feature pool. The SVM was trained for each feature type/selection method using MATLAB R2022a Statistics and Machine Learning Toolbox, with 3-fold cross-validation, different kernels (linear, polynomial, radial basis function, gaussian), different numbers of harmonics, and frequency ranges. The best model was the full PSD using the forward feature selection technique when using a linear kernel for the SVM. This model achieved an 76% average accuracy for decoding visuocortical attention toward the Gabor or the face. Using this model, feedback on where users are focusing the predominance of their attention can be provided with a high degree of confidence.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of disclosed concept which is to be given the full breadth of the claims appended and any and all equivalents thereof.

What is claimed is:

1. A system for providing neurofeedback to a user to target affect-biased attention, comprising:
an electroencephalogram (EEG) apparatus structured and configured to generate a number of EEG signals when coupled to a head of the user;
a presentation apparatus structured and configured to visually display a plurality of images to the user; and
a controller coupled to the EEG apparatus and the presentation apparatus, the controller being structured and configured to: (i) cause the presentation apparatus to display an overlaid image to the user, wherein the overlaid image comprises a first image flickering at a first frequency overlaid with a second image flickering at a second frequency different than the first frequency, the first image being an affective distractor stimulus image and the second image being a task-relevant stimulus image, (ii) receive from the EEG apparatus a number of first steady-state visual evoked potential (SSVEP) signals generated in response the first image of the overlaid image and a number of second SSVEP signals generated in response the second image of the overlaid image, and (iii) calculate feedback based on at least the number of first SSVEP signals and the number of second SSVEP signals, the feedback being indicative of how much attention of the user was allocated to the task-relevant stimulus image versus how much attention of the user was allocated to the affective distractor stimulus image, wherein the feedback is calculated using time and spectral features using one or more machine learning algorithms, wherein the spectral features are calculated through Fourier transform (FT) at competing frequency tags comprising the first frequency and the second frequency and integer multiples of each frequency, and wherein the time features are calculated time-locked to presentation of each of the images.

2. The system according to claim 1, wherein the presentation apparatus comprises an extended reality (XR) device structured and configured to be worn by the user.

3. The system according to claim 2, wherein the XR device comprises a head mounted display structured and configured to present the number of overlaid images superimposed on a real world environment of the user.

4. The system according to claim 2, wherein the EEG apparatus comprises a cap coupled to a plurality of electrodes.

5. The system according to claim 1, wherein the affective distractor stimulus image comprises an angry and/or sad face.

6. The system according to claim 1, wherein the task-relevant stimulus image comprises a visual patch or filter.

7. The system according to claim 6, wherein the visual patch or filter comprises a Gabor patch.

8. The system according to claim 1, wherein a first set of FT coefficients is determined for frequency tags comprising the first frequency and its integer multiples and a second set of FT coefficients is determined for frequency tags comprising the second frequency and its integer multiples, and wherein the feedback is based on the first and second sets of FT coefficients and time features and is indicative of a proportion of the user's attention that was allocated to the task-relevant stimulus image versus the affective distractor stimulus image.

9. The system according to claim 8, wherein the feedback includes an SSVEP competition score ranging from 0 to 1.

10. The system according to claim 9, wherein an SSVEP competition score of greater than 0.5 indicates that more attention was paid by the user to the task-relevant stimulus image as compared to the affective distractor stimulus image.

11. A system for providing neurofeedback to a user to target affect-biased attention, comprising:

an electroencephalogram (EEG) apparatus structured and configured to generate a number of EEG signals when coupled to a head of the user;

a presentation apparatus structured and configured to visually display a plurality of images to the user; and a controller coupled to the EEG apparatus and the presentation apparatus, the controller being structured and configured to: (i) cause the presentation apparatus to display an overlaid Image to the user, wherein the overlaid image comprises a first image flickering at a first frequency overlaid with a second image flickering at a second frequency different than the first frequency, the first image being an affective distractor stimulus image and the second image being a task-relevant stimulus image, (ii) receive from the EEG apparatus a number of first steady-state visual evoked potential (SSVEP) signals generated in response the first image of the overlaid image and a number of second SSVEP signals generated in response the second image of the overlaid image, and (iii) calculate feedback based on at least the number of first SSVEP signals and the number of second SSVEP signals, the feedback being indicative of how much attention of the user was allocated to the task-relevant stimulus image versus how much attention of the user was allocated to the affective distractor stimulus image, the system being structured and configured to provide the neurofeedback based on a plurality of levels of stimulus, wherein an opacity of the task-relevant stimulus image is different for each level, wherein each level comprises a plurality of epochs, and wherein each epoch comprises a plurality of trials, and wherein steps (i), (ii) and (iii) are performed for each trial to calculate the feedback for each trial.

12. The system according to claim 11, wherein the controller is structured and configured to, for each level or for each epoch, calculate a composite feedback that is based on the feedback generated for each trial of the level or epoch.

13. The system according to claim 12, wherein the feedback calculated for each trial includes an SSVEP competition score ranging from 0 to 1, and wherein the composite feedback comprises a composite SSVEP competition score comprising an average of the feedbacks generated for each trial of the level or epoch.

14. A method for providing neurofeedback to a user to target affect-biased attention, comprising:

(i) displaying an overlaid image to the user, wherein the overlaid image comprises a first image flickering at a first frequency overlaid with a second image flickering at a second frequency different than the first frequency, the first image being an affective distractor stimulus image and the second image being an affective distractor stimulus image;

(ii) receiving a number of first steady-state visual evoked potential (SSVEP) signals generated in response the first image of the overlaid image and a number of second SSVEP signals generated in response the second image of the overlaid image; and (iii) calculating feedback based on at least the number of first SSVEP signals and the number of second SSVEP signals, the feedback being indicative of how much attention of the user was allocated to the task-relevant stimulus image versus how much attention of the user was allocated to the affective distractor stimulus image, wherein the feedback is calculated using time and spectral features using one or more machine learning algorithms, wherein the spectral features are calculated through Fourier transform (FT) at competing frequency tags comprising the first frequency and the second frequency and integer multiples of each frequency, and wherein the time features are calculated time-locked to presentation of each of the images.

15. The method according to claim 14, wherein the displaying comprises displaying the overlaid image to the user in extended reality.

16. The method according to claim 14, wherein the affective distractor stimulus image comprises an angry and/or sad face.

17. The method according to claim 14, wherein the task-relevant stimulus image comprises a visual patch or filter.

18. The method according to claim 17, wherein the visual patch or filter comprises a Gabor patch.

19. The method according to claim 14, wherein a first set of FT coefficients is determined for frequency tags comprising the first frequency and its integer multiples and a second set of FT coefficients is determined for frequency tags comprising the second frequency and its integer multiples, and wherein the feedback is based on the first and second sets of FT coefficients and time features and is indicative of a proportion of the user's attention that was allocated to the task-relevant stimulus image versus the affective distractor stimulus image.

20. The method according to claim 19, wherein the feedback includes an SSVEP competition score ranging from 0 to 1.

21. The method according to claim 20, wherein an SSVEP competition score of greater than 0.5 indicates that more attention was paid by the user to the task-relevant stimulus image as compared to the affective distractor stimulus image.

22. A system for providing neurofeedback to a user to target affect-biased attention, comprising:

an electroencephalogram (EEG) apparatus structured and configured to generate a number of EGG signals when coupled to a head of the user;

a presentation apparatus structured and configured to visually display a plurality of images to the user; and a controller coupled to the EGG apparatus and the presentation apparatus, the controller being structured and configured to: (i) cause the presentation apparatus to display an overlaid image to the user, wherein the overlaid image comprises a first image flickering at a first frequency overlaid with a second image flickering at a second frequency different than the first frequency, the first image being an affective distractor stimulus image and the second image being a task-relevant stimulus image, (ii) receive from the EEG apparatus a number of first steady-state visual evoked potential (SSVEP) signals generated in response the first image of the overlaid image and a number of second SSVEP signals generated response the second image of the overlaid image, and (iii) calculate feedback based on at least the number of first SSVEP signals and the number of second SSVEP signals, the feedback being indicative of how much attention of the user was allocated to the task-relevant stimulus image versus how much attention of the user was allocated to the affective distractor stimulus image, wherein the feedback is calculated using a trained support vector machine (SVM) based on EEG features comprising a full power spectral density (PSD) of the number of first SSVEP signals and the number of second SSVEP signals, wherein the SVM is optimized using a forward feature selection method, Using a linear kernel for the SVM.

23. A method for providing neurofeedback to a user to target affect-biased attention, comprising:

(i) displaying an overlaid image to the user, wherein the overlaid image comprises a first image flickering at a first frequency overlaid with a second image flickering at a second frequency different than the first frequency, the first image being an affective distractor stimulus image and the second image being an affective distractor stimulus image;

(ii) receiving a number of first steady-state visual evoked potential (SSVEP) signals generated in response the first image of the overlaid image and a number of second SSVEP signals generated in response the second image of the overlaid image; and (iii) calculating feedback based on at least the number of first SSVEP signals and the number of second SSVEP signals, the feedback being indicative of how much attention of the user was allocated to the task-relevant stimulus image versus how much attention of the user was allocated to the affective distractor stimulus image, wherein the feedback is calculated using a trained support vector machine (SVM) based on EEG features comprising a full power spectral density (PSD) of the number of first SSVEP signals and the number of second SSVEP signals, wherein the SVM is optimized using a forward feature selection method, Using a linear kernel for the SVM.

24. A method for providing neurofeedback to a user to target affect-biased attention, comprising:

(i) displaying an overlaid image to the user, wherein the overlaid image comprises a first image flickering at a first frequency overlaid with a second image flickering at a second frequency different than the first frequency, the first image being an affective distractor stimulus image and the second image being an affective distractor stimulus image;

(ii) receiving a number of first steady-state visual evoked potential (SSVEP) signals generated in response the first image of the overlaid image and a number of second SSVEP signals generated in response the second image of the overlaid image; and (iii) calculating feedback based on at least the number of first SSVEP signals and the number of second SSVEP signals, the feedback being indicative of how much attention of the user was allocated to the task-relevant stimulus image versus how much attention of the user was allocated to the affective distractor stimulus image, wherein the neurofeedback is based on a plurality of levels of stimulus, wherein an opacity of the task-relevant stimulus image is different for each level, wherein each level comprises a plurality of epochs, and wherein each epoch comprises a plurality of trials, and wherein steps (i), (ii) and (iii) are performed for each trial to calculate the feedback for each trial.

\* \* \* \* \*